(12) United States Patent
Martin

(10) Patent No.: US 7,300,466 B1
(45) Date of Patent: Nov. 27, 2007

(54) ANATOMICALLY CONFIGURED HIP LEVEL PROSTHETIC SOCKET SYSTEM

(75) Inventor: James Jay Martin, Oklahoma City, OK (US)

(73) Assignee: Scott Sabolich Prosthetics & Research, LLC, Oklahoma City, OK (US)

( * ) Notice: Subject to any disclaimer, the term of this patent is extended or adjusted under 35 U.S.C. 154(b) by 119 days.

(21) Appl. No.: 11/051,954

(22) Filed: Feb. 4, 2005

Related U.S. Application Data

(60) Provisional application No. 60/541,604, filed on Feb. 4, 2004.

(51) Int. Cl.
*A61F 2/60* (2006.01)
*A61F 2/68* (2006.01)

(52) U.S. Cl. ....................................................... 623/31

(58) Field of Classification Search ............. 623/27–37
See application file for complete search history.

(56) References Cited

U.S. PATENT DOCUMENTS

| | | | | |
|---|---|---|---|---|
| 2,048,410 A * | 7/1936 | Rowley | ........................ | 623/31 |
| 3,090,964 A * | 5/1963 | McLaurin | ..................... | 623/31 |
| 7,077,868 B2 * | 7/2006 | Perkins et al. | ................. | 623/36 |

* cited by examiner

*Primary Examiner*—Bruce Snow
(74) *Attorney, Agent, or Firm*—Martin G. Ozinga; Phillips, McFall, McCafferty, McVay & Murrah, P.C.

(57) ABSTRACT

A prosthetic hip level socket system for a user's lower torso comprising a socket fitted to the individual user's lower torso having a mounting point for an attachment, a first strap attached to the socket and a second strap attached to the socket wherein the first strap and the second strap work in cooperation to support the socket on the iliac crests of the user's lower torso.

10 Claims, 6 Drawing Sheets

ANATOMICALLY CONFIGURED HIP LEVEL PROSTHETIC SOCKET SYSTEM

CROSS-REFERENCE TO RELATED APPLICATIONS

Priority is claimed from provisional patent application U.S. Ser. No. 60/541,604, filed on Feb. 4, 2004, and incorporated by reference herein.

FIELD OF THE INVENTION

The present invention relates generally to prosthesis for hip-disarticulation level of amputation. More particularly, the present invention is a new and improved prosthetic hip level socket apparatus and system utilizing less obtrusive trim lines, increased suspension over the iliac crests and lumbar area, reduced weight and increased control of the prosthesis, and general increased comfort to the user.

DESCRIPTION OF THE KNOWN PRIOR ART

The field of prosthetics has made enormous advances in improving amputee and congenitally deformed individuals' comfort and performance in association with removably attached prosthesis. As the study of human physiology and anatomy demonstrates, the relative simple action of walking with a prosthesis involves numerous ergonomic and biomechanical complexities wherein a compromise is often found or forced between function and comfort.

The hip-disarticulation level of amputation, or higher, can result in great difficulty in using a prosthesis. Typically, due to the high level, complex issues are presented on how to provide an easily removable prostheses, like a leg assembly, that still meets functional requirements for ambulation and is still relatively comfortable enough for a user.

In the prior art, conventional hip socket technology was generally developed in the 1960's and has had little improvement from the original prosthesis. Conventional hip level prosthetics utilize a semi-rigid frame and underlying socket which circumferentially wraps around the waist of the amputee and underneath the amputation site. These sockets typically are molded about the volume of the limb and proximally wrap over the iliac crests at the waist level and are often referred to as a "bucket" configuration. They are often very bulky and heavy, which limits the amputees' functional abilities and comfort. Due to the very uncomfortable and functional problems associated with the prior art, an 85% rejection rate of use has been common. FIG. 4 has been provided generally depicting the prior art.

What is needed is a new and improved socket system that benefits the wearer by allowing much less obtrusive trim lines, increased suspension over the iliac crests and lumbar area, much less weight of the prosthesis, increased control of the prosthesis, and increased comfort. Furthermore, what is needed is a prosthesis that decreases the rate of rejection by users found in the prior art.

Although prosthetic technology has advanced in recent years, the prior art still has failed to bridge the gap between prosthetics and user demand and needs. Therefore, an extensive opportunity for design advancements and innovation remains where the prior art fails or is deficient.

SUMMARY OF THE INVENTION

In general, the present invention is a new and improved prosthetic hip level socket apparatus and system which provides comfort and functionality where the prior art fails. The present invention generally provides a prosthetic hip level socket apparatus and system utilizing less obtrusive trim lines, increased suspension over the iliac crests and lumbar area, reduced weight and increased control of the prosthesis, and increased comfort to the user.

In a preferred embodiment, the invention may comprise straps that encompass ratchet systems and adjustable sections to accommodate length and tightness of the straps. Further, the straps are affixed to an anterior frame and posterior frame by any conventional attachment means. The straps may utilize convex sections to assist in comfort and contouring about the waist of the body. They may incorporate rigid or semi-rigid supports to help hold shape and soft areas as well to provide cushioning. The hip joint may attach to the distal end of the anterior frame utilizing conventional attachment means or utilizing a hip plate attachment means. The medial aspect of the socket (interior cavity of the frame) may contour around the ischial/ramus complex, the anus area, and the pubis/genatalia area. The posterior frame may be wide enough to encompass the posterior superior iliac spines. It is contemplated that the strap may utilize further contouring over the iliac crest location. It is further contemplated that the frame may be customized to the specific user wherein the above description is individualized to user specifications. Still further, the strap convex sections may be customized such that it is individualized to the user specifications.

In this respect, before explaining at least one embodiment of the invention in detail, it is to be understood that the invention is not limited in this application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

Accordingly, titles, headings, chapter names, classifications and overall segmentation of the application in general should not be construed as limiting. Such are provided for overall readability and not necessarily as literally defining text or material associated therewith.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved prosthetic hip level socket apparatus and system utilizing less obtrusive trim lines, increased suspension over the iliac crests and lumbar area, reduced weight and increased control of the prosthesis, and increased comfort to the user.

It is a further object of the present invention to provide a new and improved prosthetic hip level socket apparatus and system which is a relatively simple design with few parts and thus may be easily and efficiently manufactured.

An even further object of the present invention is to provide a new and improved prosthetic hip level socket apparatus and system which is of a more durable and reliable construction than that of the existing known art.

Still another object to the present invention to provide a new and improved prosthetic hip level socket apparatus and system which is susceptible of a low cost of manufacture with regard to both materials and labor, which accordingly is then susceptible of low prices of sale to the consuming public, thereby making such economically available to those in need of such prosthetic devices.

Another object of the present invention is to provide a new and improved prosthetic hip level socket apparatus and system which provides some of the advantages of the prior art, while simultaneously overcoming some of the disadvantages normally associated therewith.

Yet another object of the present invention to provide a new and improved prosthetic hip level socket apparatus and system that is well suited for most hip disarticulation amputees or given birth need.

Still yet another object of the present invention is to provide a new and improved prosthetic hip level socket apparatus and system that reduces the current rejection rate of high level amputees.

A further object of the present invention is to provide a new and improved prosthetic hip level socket apparatus and system that is generally more cosmetic in nature and cooler to use than the conventional prior art.

Still another object of the present invention is to provide a new and improved prosthetic hip level socket apparatus and system that utilizes a micro frame configuration and, therefore, gives a user greater range of motion and generally more comfort.

Another object of the present invention is to provide a new and improved prosthetic hip level socket apparatus and system that provides a user with a prosthesis that does not resemble a "bucket" approach or the limitations of such configuration.

An even further object of the present invention is to provide a new and improved prosthetic hip level socket apparatus and system that easily may be adapted to individual user's specifications and dimensions.

Still further, an object of the present invention is to provide a new and improved prosthetic hip level socket apparatus and system that provides superior support needed for use of multiple artificial joints associated with high level amputations, such as artificial hip, knee and ankle joint configurations. Furthermore, additional suspension may be established through the anatomical contouring of the socket about the wearer's underlying pelvic structure.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference would be had to the accompanying drawings and descriptive matter in which there are illustrated preferred embodiments of the invention.

BRIEF DESCRIPTION OF THE DRAWINGS AND PICTORIAL ILLUSTRATIONS

The invention will be better understood and objects other than those set forth above will become apparent when consideration is given to the following detailed description thereof. Such description makes reference to the annexed pictorial illustrations, graphs, drawings, and appendices wherein.

DETAILED DESCRIPTION OF THE PREFERRED EMBODIMENTS

Figure 1:
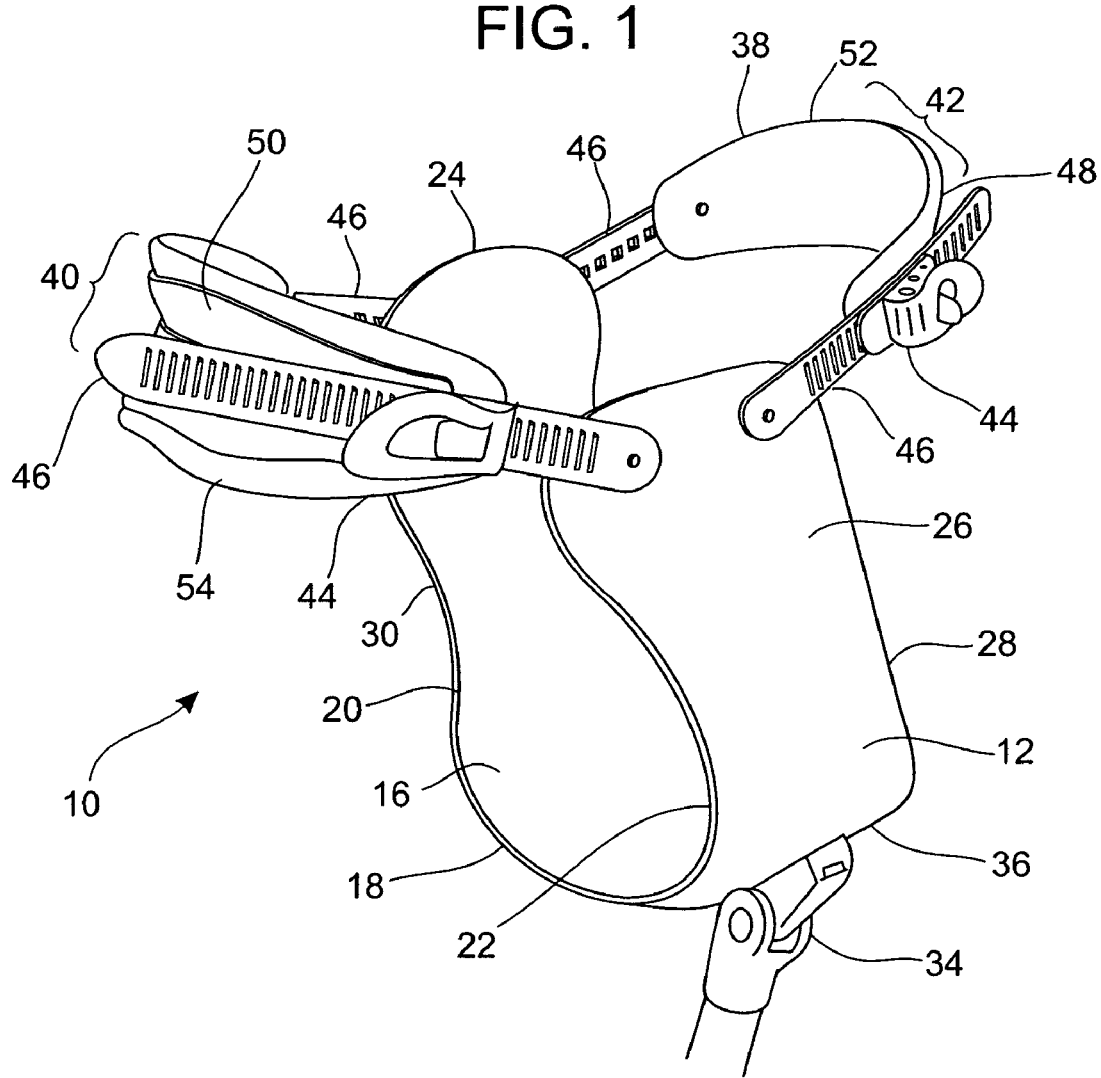
FIG. 1 is a general perspective view of a preferred embodiment of the invention.
Figure 1A:
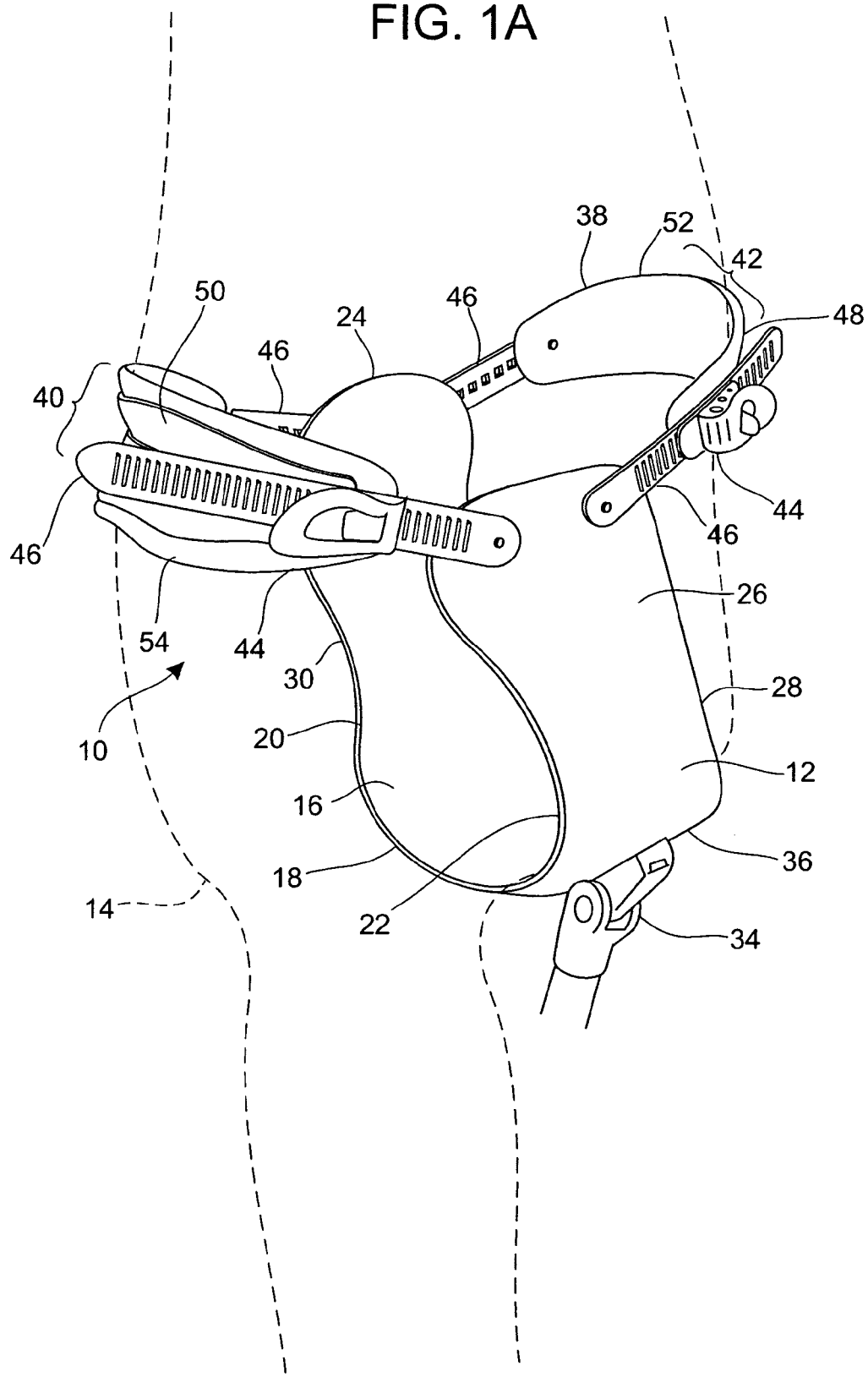
FIG. 1A is a general perspective view of a preferred embodiment of the invention also generally depicting the lower torso of a human using the invention.
Figure 2:
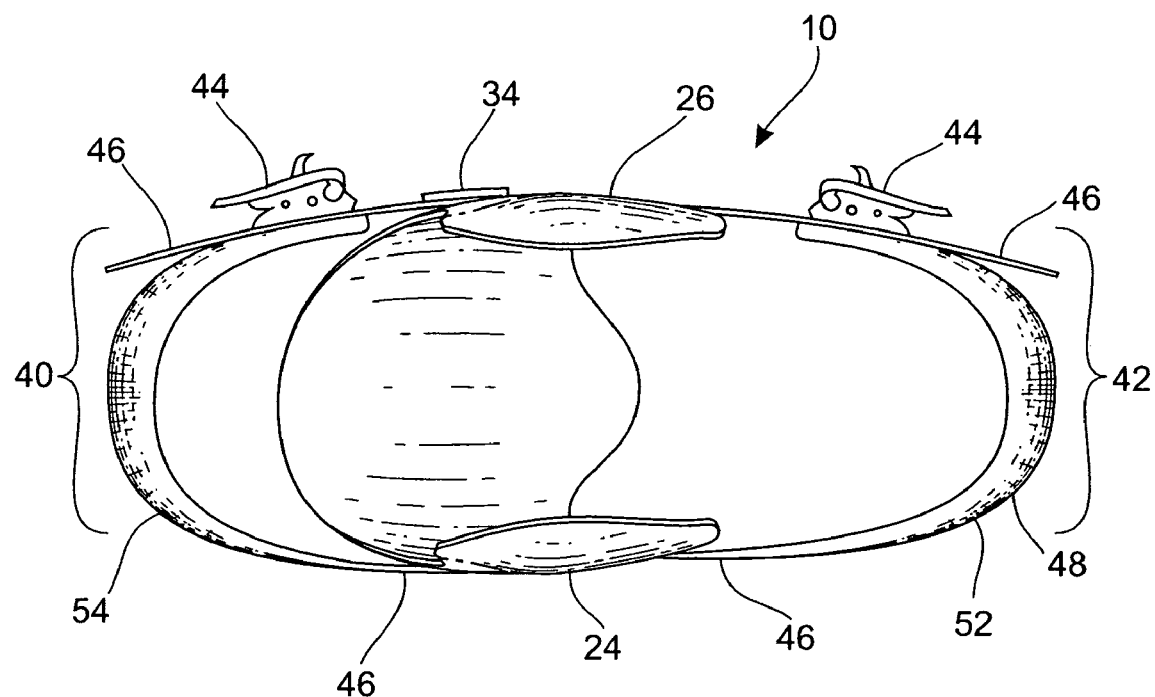
FIG. 2 is a general top view of a preferred embodiment of the invention generally depicted in FIG. 1.

Referring now to the drawings, wherein like reference numerals designate corresponding structure throughout the views, and referring in particular to FIGS. 1 and 2, reference numeral 10 generally refers to a new and improved anatomically configured hip level prosthetic socket apparatus, assembly and/or system in accordance with the present invention, hereinafter referred to generally and collectively as invention 10.

Of note, invention 10 is generally shown in a configuration for an individual missing a right leg or portion thereof at a hip level. It is understood that such configuration is for example purposes only and that such should not be considered limiting and a left side configuration is also considered. It is further understood that invention 10 may be used where the level of amputation may dictate a different configuration. The terms should not be considered limiting the invention nor the general shape and configuration depicted in the drawings.

In a preferred construction, a socket 12 is utilized. The socket 12 shape will generally contour around the anatomy of body 14. The interior cavity 16 or medial aspect of socket 12 may contour around the ischial/ramus complex 18, the anus area 20, and the pubis/genatalia area 22. The posterior frame 24 should be wide enough to encompass the posterior superior iliac spines.

Figure 3:
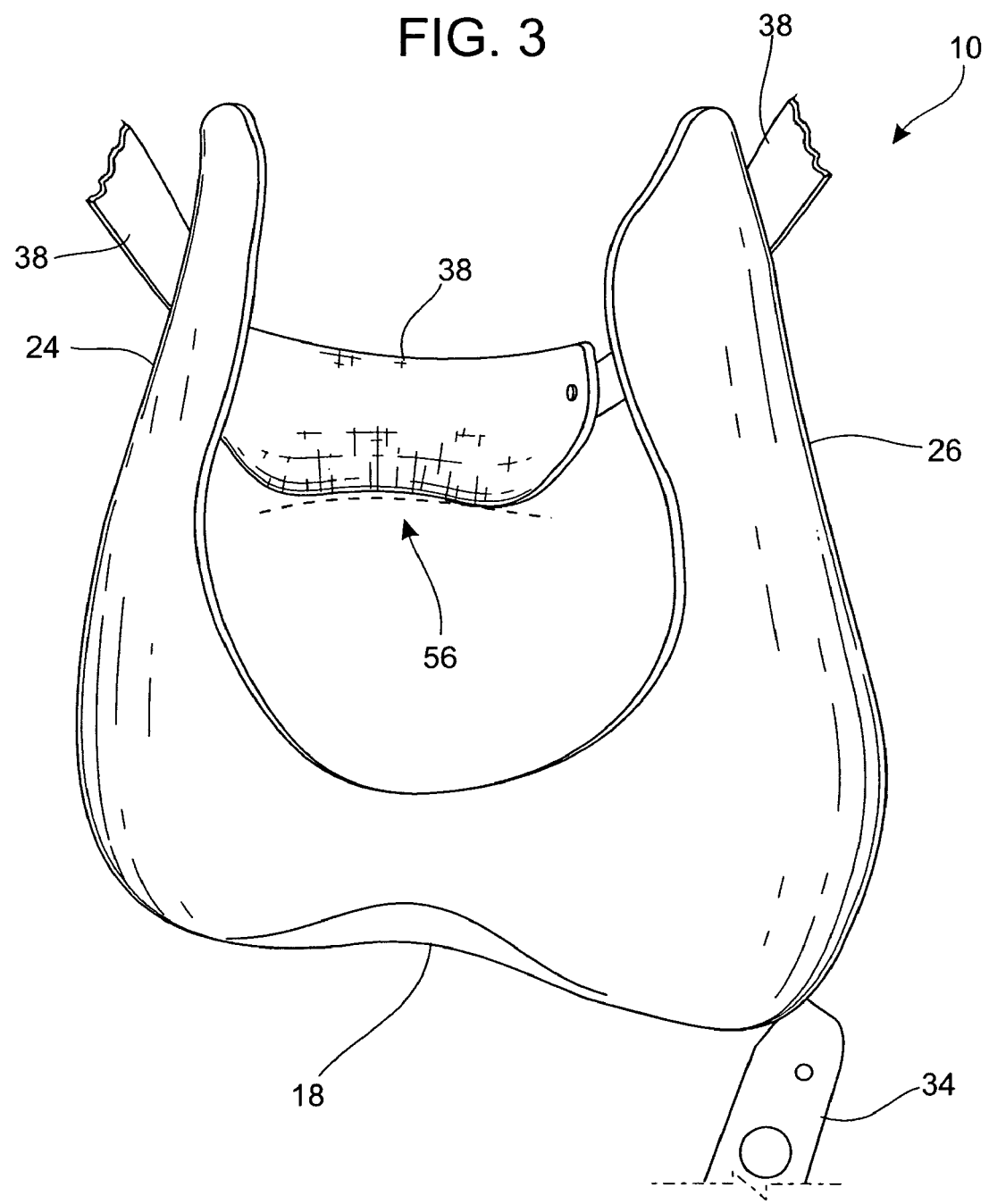
FIG. 3 is a general side view of a preferred embodiment of the invention generally depicted in FIG. 1.
Figure 4:
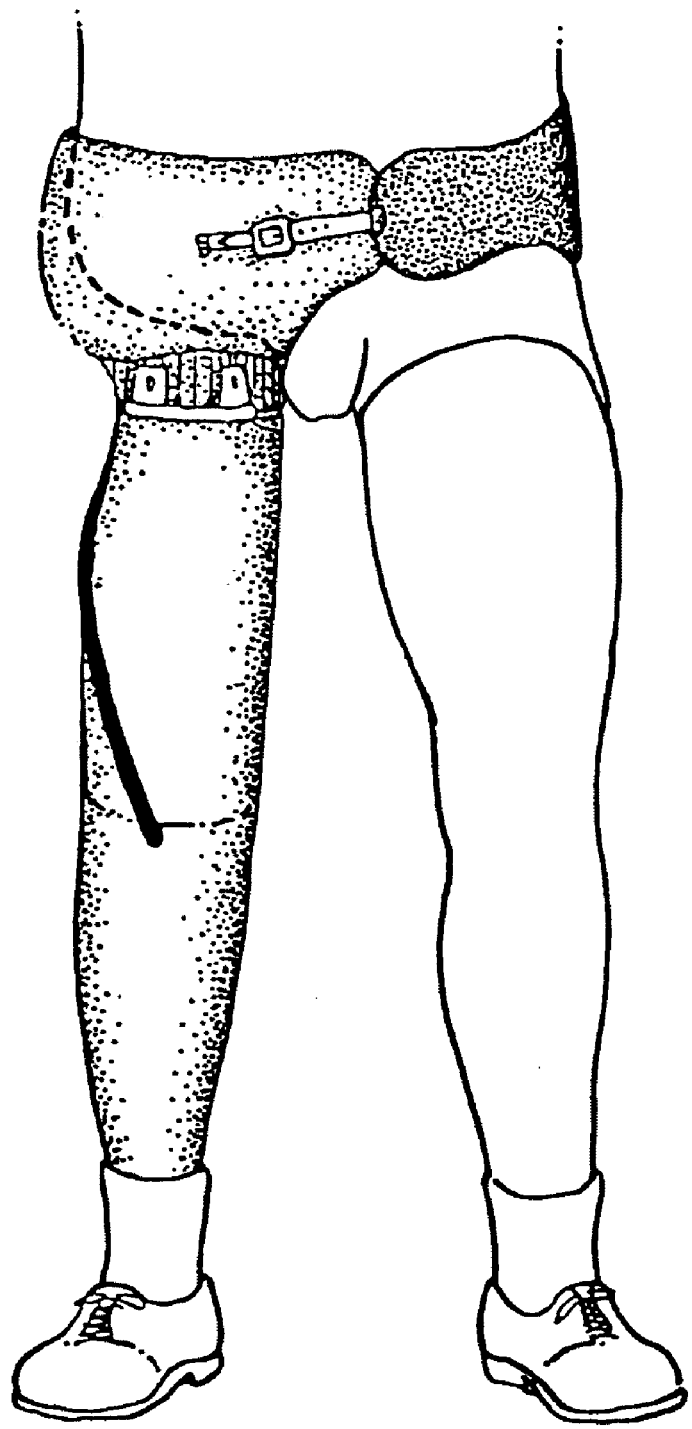
FIG. 4 is a general illustration of the prior art.

Referring again to the drawings and in particular FIG. 3, socket 12 is generally illustrated depicting that the posterior frame 24 wherein it may come up high enough to cup up over the lower lumbar spine. FIG. 2 generally depicts how the anterior frame 26 and posterior frame 24 may be relatively parallel.

Distally, if the amputee has an ischial/ramus complex, the medial aspect of socket 12 may contour about it to help provide distal medial/lateral support. The anterior trim line 28 and posterior medial trim line 30 of socket 12 may contour lateral to the genitalia and anus. The lateral aspect of the trim lines may be cut at around the mid-hip level, in order to provide medial/lateral support from the lateral aspect of the ileum. Proximal anterior and proximal posterior areas may contour in about the wearers abdominal region and lumbar, posterior superior iliac spine, and gluteal regions respectively.

It is contemplated that anterior frame 26 and posterior frame 24 may generally be configured like rigid struts in order to maintain anterior/posterior support of the pelvis in socket 12 for a controlled anterior/posterior dimension. It is contemplated that this anterior/posterior dimension may also be adjustable to allow for volumetric fluctuations of the body. The socket 12 may utilize corrugations or contouring in these areas to additionally prevent excessive flex of anterior/posterior dimensions. In a preferred embodiment, these areas would be relatively centered medial/laterally about the waist. This type of socket 12 may as well be utilized on a very short trans-femoral amputee who often requires being fit like a hip level amputee would be fit prosthetically.

The materials for socket 12 may be made of thermoplastics, thermosets, laminates such as but not limited to carbon fiber or fiberglass materials, or other semi-rigid materials. In a preferred embodiment an inner socket 32 (not shown) may be utilized which would generally fit inside socket 12 which may be made of any material that is rigid to flexible, but for the wearer's comfort, preferably flexible in nature. In a preferred embodiment, it may utilize a flexible or semi-flexible inner socket with a rigid or semi-rigid frame. The inner socket will benefit the wearer by allowing increased adjustability to the system as a whole, as well as providing increased cushioning and comfort.

In accordance with a preferred embodiment of the invention, socket 12 may be removably connected to an attachment such as but not limited a prosthetic hip joint 34. Any conventional hip joints may be utilized with this system. Additionally, in a preferred embodiment, hip joint 34 may be utilized wherein a hip plate (not shown) is positioned on the inside of the lamination or socket 12. With this system, hip joint 34 would be bolted or fixedly connected to a rigid plate on the back side of the frame system. Hip joint 34 attaches to the mounting point or distal end 36 of socket 12 anterior frame 24 utilizing conventional attachment means or utilizing a hip plate attachment means. It is understood that numerous means may be contemplated for the physical attachment of socket 12 to hip joint 34 or that other attachments other than hip joint 34 may be utilized.

In accordance with a preferred embodiment, attached to the anterior frame 26 and posterior frame 24 are adjustable straps system 38 which may include a first strap 40 and second strap 42. The semi-flexible strap system 38 may encompass a ratchet or ratchet systems 44 and adjustable sections 46 to accommodate length and tightness of straps system 38. They are generally connected to the anterior frame 26 and posterior frame 24 of socket 12 by any conventional attachment means. The straps system 38 may utilize convex sections 48 and 50 to assist in comfort and contouring about the waist of body 14. They may incorporate rigid or semi-rigid supports 52 and 54 to help hold shape and soft areas as well to provide cushioning. It is further contemplated that these supports 52 and 54 may be general padding material. Straps system 38 may generally utilize contouring over the iliac crest location 56.

Figure 5:
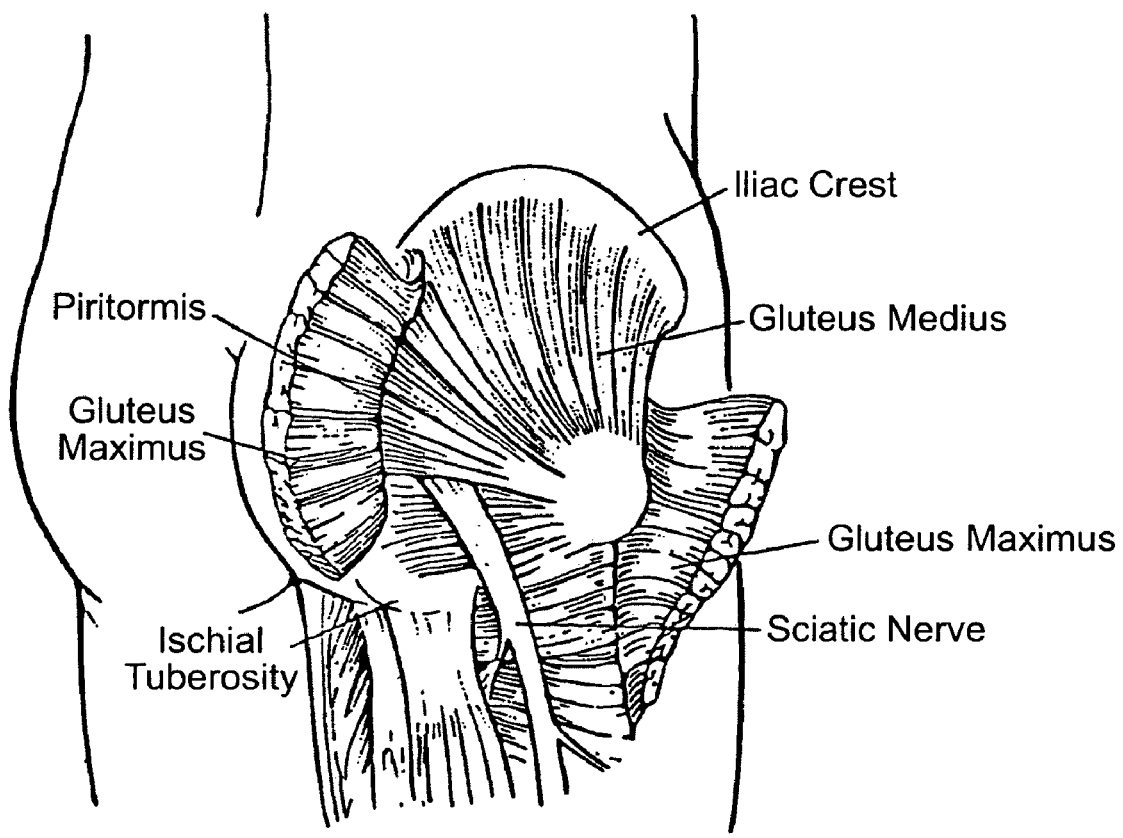
FIG. 5 is a general illustration of the human anatomy depicting the location of the iliac crest.

In a preferred embodiment, straps system 38 may utilize ratchet 44 mechanisms to enable the wearer to progressively tighten down first strap 40 adjustable length and second strap 42 adjustable length over the iliac crests respectively. Straps system 38 may utilize convex padding for additional comfort for the wearer. In a preferred embodiment, it may have a slight proximal arc over the iliac crest itself as a relief for this bony prominent area. FIG. 5 has generally been provided to illustrate the human anatomy and the iliac crest.

It is understood that straps system 38 may be adjustable in the front and in the back or generally an adjustable length utilizing any conventional adjustability means. The adjustability may allow straps system 38 to be altered at an angle from 90 degrees relative to the vertical midline of body 14, to 145 degrees. It is understood that they may be adjusted in length, placement of the pads, or alignment in any axis.

The straps system 38 materials may be fabricated out of any semi-flexible material or combination of materials. It is contemplated that a design may be similar to ski boot binding straps in nature in that it may utilize form contoured sections to hold shape while utilizing softer, more pliable sections for comfort where needed. Additionally, the adjustability sections 46 may use rubber, plastic or other materials that will allow adjustments of the tightness of the individual strap sections about the hips.

Of note, in conventional hip level socket systems, the area that tightens around the waist pulls circumferentially about the entire prosthesis. This is limiting because it prevents optimal contouring about the iliac crests specifically (which is the main suspension area for this level of prosthesis). With the current invention 10, the lateral straps may be specifically isolated to contour about the iliac crests to optimize comfort and suspension abilities. Therefore, first strap 40 may be attached to socket 12 and second strap 42 may be attached to socket 12 wherein first strap 40 and second strap 42 work in cooperation to support socket 12 on or about the iliac crests of a user's lower torso.

While the invention has been described with a certain degree of particularity, it is manifest that many changes may be made in the details of construction and the arrangements of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled. Accordingly, other implementations are within the scope of the following claims. Changes may be made in the combinations, operations, and arrangements of the various parts and elements described herein without departing from the spirit and scope of the invention.

I claim:

1. A prosthetic hip level socket system for a user's lower torso comprising:
    a socket fittable to said user's lower torso below the right iliac crest and the left iliac crest, having a mounting point for an attachment, a rigid anterior frame, and a rigid posterior frame;
    a semi rigid first strap attached to said socket anterior frame and said socket posterior frame wherein said first strap is adapted to fit over the right iliac crest of said user's lower torso; and
    a semi rigid second strap attached to said socket anterior frame and said socket posterior frame wherein said second strap is adapted to fit over the left iliac crest of said user's lower torso.

2. The prosthetic hip level socket system of claim 1 wherein said first strap has an adjustable length.

3. The prosthetic hip level socket system of claim 2 wherein said second strap has an adjustable length.

4. The prosthetic hip level socket system of claim 3 wherein said socket is made from fiberglass.

5. The prosthetic hip level socket system of claim 3 wherein said socket is made from carbon fiber.

6. The prosthetic hip level socket system of claim 1 wherein said attachment is a prosthetic hip joint.

7. The prosthetic hip level socket system of claim 6 wherein said attachment is a removably attached prosthetic hip joint.

8. The prosthetic hip level socket system of claim 1 wherein said socket is contoured around the ischial/ramus complex, the anus area, and the pubis/genetalia area.

9. The prosthetic hip level socket system of claim 1 wherein said first strap includes convex padding.

10. The prosthetic hip level socket system of claim 9 wherein said second strap includes convex padding.

* * * * *